(12) United States Patent
Yoon et al.

(10) Patent No.: US 10,328,113 B2
(45) Date of Patent: Jun. 25, 2019

(54) METHOD FOR PREVENTING OR TREATING AN ALLERGIC DISEASE USING EXTRACT FROM ILLICIUM VERUM

(75) Inventors: TaeSook Yoon, Seoul (KR); Yoon-Young Sung, Daejeon (KR); Won-Kyung Yang, Daegu (KR); Ho Kyoung Kim, Daejeon (KR)

(73) Assignee: Korea Institute of Oriental Medicine, Daejeon (KR)

( * ) Notice: Subject to any disclaimer, the term of this patent is extended or adjusted under 35 U.S.C. 154(b) by 0 days.

(21) Appl. No.: 13/562,520

(22) Filed: Jul. 31, 2012

(65) Prior Publication Data

US 2014/0037761 A1 Feb. 6, 2014

(51) Int. Cl.

| | | |
|---|---|---|
| *A61K 36/79* | (2006.01) | |
| *A61K 8/97* | (2017.01) | |
| *A61K 9/00* | (2006.01) | |
| *A61K 47/10* | (2017.01) | |
| *A61Q 19/00* | (2006.01) | |
| *A23L 33/105* | (2016.01) | |

(52) U.S. Cl.
CPC ............ *A61K 36/79* (2013.01); *A23L 33/105* (2016.08); *A61K 8/97* (2013.01); *A61K 9/0014* (2013.01); *A61K 47/10* (2013.01); *A61Q 19/00* (2013.01); *A61K 2800/75* (2013.01)

(58) Field of Classification Search
None
See application file for complete search history.

(56) References Cited

FOREIGN PATENT DOCUMENTS

| | | | |
|---|---|---|---|
| CN | 101612369 A | * | 12/2009 |
| KR | 20110067216 A | * | 6/2011 |
| KR | 10-2012-0010984 A | | 2/2012 |
| WO | WO03084522 A1 | * | 10/2003 |

OTHER PUBLICATIONS

Mayoclinic 2011 http://www.mayoclinic.com/health/eczema/DS00986.*
Soap Queen, 2011 http://www.soapqueen.com/bramble-berry-news/essential-oil-feature-star-anise/.*
Wang et al., Illicium verum: A review on its botany, traditional use, chemistry and pharmacology, 2011, J Ethnopharmacology, 136: 10-20.*
NIH 2012, https://newsinhealth.nih.gov/issue/apr2012/feature1.*
Dajee et al., Blockade of Experimental Atopic Dermatitis via Topical NF-jB Decoy Oligonucleotide, 2006, J Investigative Dermatology, 126: 1792-1803.*
Chainy et al., Anethole blocks both early and late cellular response transduced by tumor necrosis factor: effect on NF-kB, AP-1, JNK, MAPKK and apoptosis, 2000, Oncogene, 19: 2943-2950.*
De et al., Antimicrobial Properties of Star Anise (Illicium verum Hook f), 2002, Phytother Res, 16: 94-95.*
Kim et al., "*Lithospermi radix* Extract Inhibits Histamine Release and Production of Inflammatory Cytokine in Mast Cells," Biosci. Biotechnol. Biochem. 71:2886-2892, 2007.
Oshio et al., "*Dermatophagoides farinae* Extract Induces Severe Atopic Dermatitis in NC/Nga Mice, which is Effectively Suppressed by the Administration of Tacrolimus Ointment," Int. Immunopharmacol. 9:403-411, 2009.
Yamamoto et al., "A Novel Atopic Dermatitis Model Induced by Topical Application with *Dermatophagoides farinae* Extract in NC/Nga Mice," Allergology Int. 56:139-148, 2007.

\* cited by examiner

*Primary Examiner* — Terry A McKelvey
*Assistant Examiner* — Catheryne Chen
(74) *Attorney, Agent, or Firm* — Clark & Elbing LLP; Susan M. Michaud (57) ABSTRACT

The present invention provides a method for preventing or treating an allergic disease, comprising administering to a subject a composition comprising an extract from *Illicium verum* as an active ingredient. The extract from *Illicium verum* of the present invention reduces the secretion amount of increased histamine by compound 48/80 and the production amount of the increased allergenic cytokines (TNF-α, IL-4 and IL-8) by PMA and A23187. The *Illicium verum* extract of the present invention reduces edema, dermatitis and IgE concentration of serum in atopic dermatitis mouse model. The *Illicium verum* extract of the present invention may be efficiently use for prevention, improvement or treatment of various allergic disease such as edema, hypersensitivity, contact dermatitis, atopic dermatitis, skin allergy, asthma or urticaria as pharmaceutical compositions, skin external applications, cosmetic compositions or food compositions.

20 Claims, 5 Drawing Sheets

METHOD FOR PREVENTING OR TREATING AN ALLERGIC DISEASE USING EXTRACT FROM ILLICIUM VERUM

BACKGROUND OF THE INVENTION

Field of the Invention

The present invention relates to a method for preventing or treating an allergic disease using an extract from *Illicium verum*.

Description of the Related Art

Allergies are known as sensitive reaction which is caused by immune dysfunction innately or acquired against harmless antigen. Immune mechanisms for allergic reactions are as follows: once body is exposed to allergens, the allergens are recognized by circulating antigen-presenting cells such that antigen-presenting cells allow for differentiation to TH0 cells from TH2 cells through presenting allergens. These differentiated Th2 cells secrete allergy-induced cytokines such as TNF-α, IL-4, IL-5, IL-8 and IL-13. The cytokines promote eosinophil development in bone marrow, inducing eosinophil go to inflammation tissue and also effect to B cells, inducing production of IgE and IgG1. The produced IgE by such mechanisms binds strongly to mast cells by mediating IgE receptor which is called FcεRI in tissue. Then, when it is exposed again to same allergens and allergens bind to IgE which is bind to mast cells, the mast cells secrete allergic histamine, inflammatory prostaglandins, heparin, proteases and free radicals, they induce symptoms for various allergic diseases. If this respond continues, it induces chronic inflammation in tissue (Galli et al., The development of allergic inflammation. Nature (2008) July 24, 454(7203), 445-454).

The illustrated examples of these allergic diseases include anaphylaxis, allergic rhinitis, asthma, allergic conjunctivitis, allergic dermatitis, atopic dermatitis, contact dermatitis, urticaria, pruritus, insect allergic diseases, food allergic diseases or drug allergic diseases.

Meanwhile, allergies are different from inflammations. Concretely, inflammations involves 1) the step of stimulating monocytes or immune cells such as macrophages against damages or infections in cells and tissues, 2) the step of inducing the target cell activation and phagocytosis, 3) the step of production and secretion of proximal mediators in initial host response followed by secretion of complements or proinflammatory cytokines, 4) the step of secreting the middle mediators such as PLA2 or PGE2 by stimulating secondary target cells with the initial mediators, and 5) the step of damaging tissues or cells by secreting proteases, PAF and reactive oxygen species as distal effectors.

In other words, allergies have different main immune cells or main response factors in induced mechanism, compared with the inflammation and their response pathways are also different. In this regard, inflammatory diseases include allergic inflammatory diseases associated with allergies and non-allergic inflammatory diseases unrelated to allergies, which is included common inflammatory diseases such as various dermatitis, systemic lupus erythematosus, retinitis, gastritis, hepatitis, gastroenteritis, pancreatitis, and nephritis. Especially, non-allergic inflammatory diseases unrelated to allergies are disclosed in a variety of publications as follows: Kawase et al. (Exacerbated and prolonged allergic and non-allergic inflammatory cutaneous reaction in mice with targeted interleukin-18 expression in the skin. Journal of Investigative Dermatology (2003), September, 121(3), 502-509), Makoto Katori et al. (Roles of leukotrienes in non-allergic and allergic inflammatory models. Prostaglandins, Volume 28, Issue 5, November 1984, 617-619) and Nourshargh et al. (Accumulation of 111In-neutrophils in rabbit skin in allergic and non-allergic inflammatory reactions in vivo. Inhibition by neutrophil pretreatment in vitro with a monoclonal antibody recognizing the CD18 antigen. The Journal of Immunology (1989), May 1, 142(9), 3193-3198). In addition, anti-inflammatory effectiveness has already been reported by the prior art, including old platycodon grandiflorus (KR Pat. No. 10-0943754), Clematidis radix (KR Pat. No. 10-0857896), Aralia cordata Thunb (KR Pat. No. 10-0818363) and buckwheat (KR Pat. No. 10-0787363), but they are registered as anti-allergic composition and considered as cases to admit difference between allergies and inflammations.

In oriental medicine, Illici Veri Fructus refers to fruits of *Illicium verum* which is belongs to Illiciaceae.

*Illicium verum* has been known to treat for backache, abdominal pain and toothache and also utilize in indigestion.

Throughout this application, various patents and publications are referenced, and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

Technical Purposes of the Invention

The present inventors have made intensive efforts to develop a drug for allergic diseases without toxicities and side effects. As a result, the present inventors have found that a composition for prevention or treatment of allergic diseases containing the extract from *Illicium verum* as an active ingredient inhibits release of allergic histamine and production of allergy-induced cytokines (TNF-α, IL-4 and IL-8) and reduces edema in atopic dermatitis mouse model, dermatitis and the level of IgE in serum.

Accordingly, it is an object of this invention to provide a method for preventing or treating an allergic disease.

Other objects and advantages of the present invention will become apparent from the following detailed description together with the appended claims and drawings.

Technical Construction of the Invention

In an aspect of this invention, there is provided a method for preventing or treating an allergic disease, comprising administering to a subject a composition comprising an extract from *Illicium verum* as an active ingredient.

The present inventors have made intensive efforts to develop a drug for allergic diseases without toxicities and side effects. As a result, the present inventors have found that a composition for prevention or treatment of allergic diseases containing the extract from *Illicium verum* as an active ingredient inhibits release of allergic histamine and production of allergy-induced cytokines (TNF-α, IL-4 and IL-8) and reduces edema in atopic dermatitis mouse model, dermatitis and the level of IgE in serum.

The extract from *Illicium verum* using as an active ingredient in this present invention may be obtained from various organs or parts of *Illicium verum*. The extract may be obtained using extraction solvents known to those ordinarily skilled in the art, preferably, (a) water, (b) C1-C4 anhydrous or hydrous lower alcohol (e.g., methanol, ethanol, propanol, butanol, n-propanol, isopropanol, n-butanol, etc.), (c) a mixture solvent of the lower alcohol with water, (d) acetone, (e) ethylacetate, (f) chloroform, (g) 1,3-butylene glycol, (h) hexane, (i) diethyl ether or (j) butyl acetate may be used for obtaining.

The suitable amount of the extraction solvent is 1-20 folds (preferably, 1-10 folds) of the dry weight of *Illicium verum*.

*Illicium verum* is washed with distilled water, dried, pulverized and added 1-10 fold extraction solvents. The resultant is subjected to extraction by heating at 400-100° C. for 3-20 hr or at 4-40° C. for 1-15 days using a cooled condenser for preventing evaporation of active ingredients, and then completely dried using a rotary vacuum evaporator. Meanwhile, it is difficult to dry 1,3-butylene glycol using a rotary vacuum evaporator. Where 1,3-butylene glycol is used, the extract is processed to ensure the dry weight to be 1% (w/v) with no use of a rotary vacuum evaporator.

Meanwhile, it is clear to a skilled artisan that the extracts of the present invention having substantially similar effects may be obtained using other extraction solvents as well as the extraction solvents described above.

Moreover, the extract of the present invention includes any extract by common purification process as well as the extraction by above described the extraction solvent. For example, the purification process includes fractions which obtained by passing the plant extract through an ultrafiltration membrane with a predetermined molecular weight cut-off value, separating through various chromatographic (based on size, charge, hydrophobicity or affinity) techniques, and purifying through various methods.

The *Illicium verum* extract of the present invention may be prepared in the form of powder by additional processing such as distillation under reduced pressure, lyophilization and spray drying.

The composition of the present invention significantly exhibits prevention, treatment or improvement efficacies on allergic diseases.

As used herein the term "prevention" refers to delaying or forestalling the onset or development of allergic diseases by administration of the present composition.

As used herein, the term "treatment" refers to (a) inhibition of the development of allergic diseases; (b) alleviation of allergic diseases; and (c) elimination of allergic diseases.

As used herein, the term "improvement" refers to amelioration or lessening of allergic diseases by administration of the present composition.

According to a preferable embodiment of the present invention, the allergic disease prevented or treated by the composition of the present invention is selected from the group consisting of edema, anaphylaxis, allergic rhinitis, asthma, allergic conjunctivitis, allergic dermatitis, atopic dermatitis, contact dermatitis, urticaria, pruritus, insect allergy, alimentary allergy, and drug allergy, but not limited to.

The composition of the present invention may be a pharmaceutical composition for preventing or treating allergic diseases, comprising an extract from *Illicium verum* as an active ingredient.

When the composition of the present invention is prepared as a pharmaceutical composition, the pharmaceutical composition of the present invention may comprise a pharmaceutically acceptable excipient. The pharmaceutically acceptable excipient included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present invention may further include, in addition to above-described components, a lubricant, a wetting agent, a sweetener, a fragrance, an emulsifier, a suspending agent, a preservative, or the like. Suitable pharmaceutically acceptable excipients and formulations are described in detail in Remington's Pharmaceutical Sciences (19th ed., 1995).

The pharmaceutical composition of the present disclosure may be administered orally or parenterally. The parenteral administration includes intravenous injection, subcutaneous injection, intramuscular injection and intraarticular injection.

An appropriate dosage of the pharmaceutical composition of the present invention may be determined variously depending on such factors as preparation method, administration method, age, body weight and sex of the patient, pathological condition, diet, administration time, administration route, excretion rate or response sensitivity. Specifically, the dosage of the pharmaceutical composition of the present invention for an adult may be 0.001-1000 mg/kg.

The pharmaceutical composition of the present invention may be prepared into a unit dosage form or multiple dosage form along with a pharmaceutically acceptable excipient and/or carrier according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

The carrier may includes purified water, monohydric alcohols (e.g., ethanol or propyl alcohol), polyalcohols (e.g., glycerol, 1,3-butylene glycol or propylene glycol), high quality fatty acid (e.g., palmitic acid or linolenic acid), fat and oils (e.g., wheat germ oil, camellia oil, jojoba oil, olive oil, squalane, sunflowers oil, macadamia nut oil, avocado oil, soy bean hydrogenated lecithin or fatty acid glyceride), but not limited to. And, detergents, germicides, anti-oxidants, ultraviolet ray absorbents, anti-inflammatory or refresher are added as occasion demands.

The detergent may be selected from the group includes polyoxyethylene, hydrogenated castor oil, oleyl ether, monooleic acid polyoxyethylene, polyoxyethylene, glyceryl monostearate, monostearic acid sorbitan, sorbitan, sucrose fatty acid ester, monolauric acid hexaglycerin, hydrogenated lanolin, POE, glycerylpyroglutamic acid, isostearic acid, N-acetylglutamine and isostearylester.

The germicides may be selected from the group includes hinokitiol, triclosan, chlorhexidine gluconate, phenoxyethanol, resorcin, isopromethyiphenol, azulene, salicylic acid and zinc pyritaon.

The anti-oxydants may be use any anti-oxydants from the group includes butylhydroxyanisol, gallic acid, propyl gallate benzoic acid and arythorbate.

The ultraviolet ray absorbents may be use any ultraviolet ray absorbent from benzophenones of dihydroxybenzophenone, melanine, p-aminobenzoic acid ethyl, p-dimethylaminobenzoic acid, 2-ethylhexylester, cinoxate, p-methoxycinnamic acid, 2-ethylhexylester, 2-(2-hydroxy-5-methylphenyl)benzotriazole, urocanic acid and metal hydrate particles.

The anti-inflammatory may be use dipotassium glycyrrhizinate or allantoin and refresher may be use capsicum tincture or 1-menthol.

The composition of the present invention may be a cosmetic composition or topical composition for preventing, treating or improving allergic diseases, comprising an extract from *Illicium verum* as an active ingredient.

When the composition of the present invention is obtained as a skin external application or a cosmetic composition, the skin external application or the cosmetic composition of the present invention may comprise cosmetically acceptable excipients such as an adjuvant as anti-oxidants, stabilizers, solvent, vitamins, pigments, and flavors, and carriers. Moreover, the composition of the present invention comprises common moisturizers, sealants and humectants with ceramide in the range of no damage to the action (prevention or treatment of the allergic disease by the extract from *Illicium verum*) except the *Illicium verum* extract.

The cosmetic compositions of this invention may be formulated in a wide variety of forms, for example, including a solution, a suspension, an emulsion, a paste, a gel, a cream, a lotion, a powder, a soap, a surfactant-containing cleanser, an oil, a powder foundation, an emulsion foundation, a wax foundation and a spray but not limited to. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycol, silicone, bentonites, silica, talc or zinc oxide.

In the formulation of powder or spray, it may comprise lactose, talc, silica, aluminum hydroxide, calcium silicate or polyamide powder. Spray may additionally comprise the customary propellants, for example, chlorofluorohydrocarbons, propane/butane or dimethyl ether.

The formulation of solution and emulsion may comprise solvent, solubilizer and emulsifier as the carrier ingredient, for example water, ethanol, isopropanol, ethyl carbonate, ethyl acetate, benzyl alcohol, benzyl benzoate, propylene glycol, 1,3-butylglycol, glycerol fatty esters, polyethylene glycol or fatty acid esters of sorbitan.

The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum meta-hydroxide, bentonite, agar or tragacanth as the carrier ingredient.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives or ethoxylated glycerol fatty acid ester.

The composition of the present invention may be a food composition for preventing or improving allergic diseases, comprising an extract from *Illicium verum* as an active ingredient.

The composition of the present invention may be provided as a food composition, particularly a functional food composition. The food composition of the present invention may comprise common acceptable ingredients as well as the *Illicium verum* extract, for example, including proteins, carbohydrates, fatty acids, nutrients, seasoning agents and flavoring agents. The examples of carbohydrates, for examples, monosaccharide (e.g., glucose and fructose); disaccharide (e.g., maltose, sucrose and oligosaccharide); and polysaccharide (e.g., dextrin and cyclodextrin); and sugar alcohol (e.g., xylitol, sorbitol and erithritol). Favoring agent may use the natural flavoring agents [e.g., thaumatin and stevia extract (e.g., rebaudioside A and glycyrrhizin)] and the synthetic flavoring agents (saccharine and aspartames).

Non-limiting examples of food composition be used composition of the present invention. The various food composition comprising the *Illicium verum* extract of the present invention includes meats, sausages, breads, chocolates, candies, snacks, crackers, pizzas, instant noodles, noodles, gums, dairy products comprising ice creams, all sorts of soups, drinking water, tea, drinks, alcoholic drinks and vitamin mixture etc. and it all includes the food as a common meanings.

For example, where the food composition of this invention is provided as a drink, it may further comprise citric acid, high fructose corn syrup, sugar, glucose, acetic acid, mac acid, fruit juice, *Eucommia ulmoides* oliver extract, jujube extract or *Glycyrrhiza* extract.

Advantageous Effects of the Invention

The features and advantages of the present invention will be summarized as follows:

(i) The *Illicium verum* extract of the present invention reduces the secretion amount of increased histamine by compound 48/80 and the production amount of the increased allergenic cytokines (TNF-$\alpha$, IL-4 and IL-8) by PMA and A23187.

(ii) The *Illicium verum* extract of the present invention reduces edema, dermatitis and IgE concentration of serum in atopic dermatitis mouse model.

(iii) The *Illicium verum* extract of the present invention may be efficiently use for prevention, improvement or treatment of various allergic disease such as edema, hypersensitivity, contact dermatitis, atopic dermatitis, skin allergy, asthma or urticaria as pharmaceutical compositions, skin external applications, cosmetic compositions or food compositions.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Preparation of *Illicium verum* Extract 300 g of *Illicium verum* purchased from Jeongdo Pharmacy, Inc. (Korea) was dried and pulverized, followed by adding 10 volume of 70% ethanol solution and stirring well. The resultant was reflux-extracted twice for 2 hr at 50-60° C. and then filtered through a filter paper. The extract was concentrated at 50-55° C. under vacuum using a concentrator and lyophilized to obtain 70%-ethanol extract (47.19 g).

Experimental Example 1

Analysis of Cytotoxicity of *Illicium verum* Extract 1-1. Cell Culture

Mouse mast cells, MC/9 (American Type Culture Collection: ATCC, Rockville, USA), were cultured at 37° C. and under 5% $CO_2$ atmosphere in DMEM medium supplemented with heat-inactivated 10% FBS (Fetal Bovine Serum), 100 units/ml penicillin and 100 μg/ml streptomycin.

1-2. Cytotoxicity Test

For analyzing cytotoxicity of *Illicium verum* extract, we performed Cell Counting kit-8 (CCK-8) assay. MC/9 mast cells were seeded in a 96-well plate, incubated with the *Illicium verum* extract in concentrations of 0, 25, 50, 100, 200, and 400 μg/ml and cultured for 24 hr. After incubating with 10% CCK-8 for 2 hr at 37° C., we measured the absorbance at 450 nm using a Microplate spectrophotometer (Biorad, Hercules, USA) and calculated the relative viability (%) by comparing with the control group.

Figure 1:
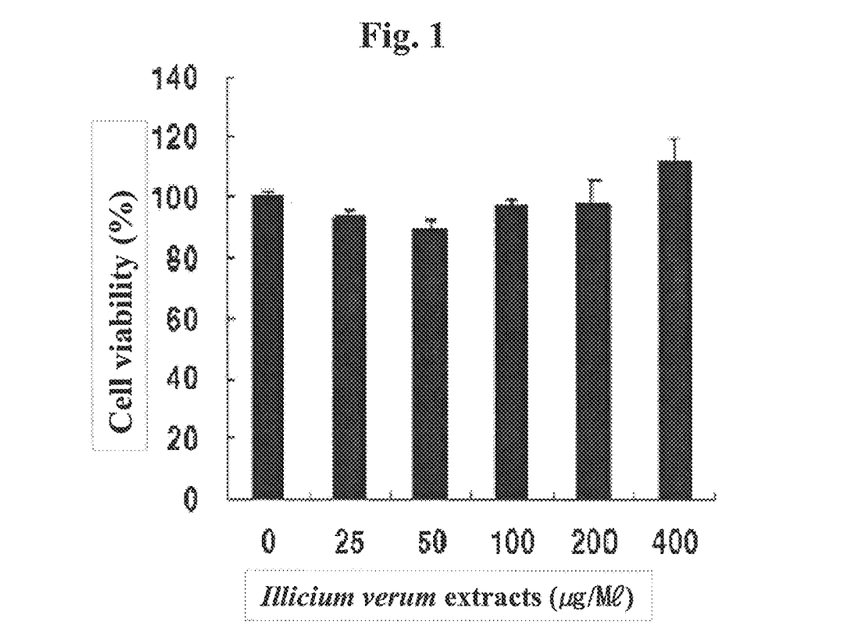
FIG. 1 represents cytotoxicity of the *Illicium verum* extract.

As a result, it was evaluated that the *Illicium verum* extract has little or no cytotoxicity with viability of more than 80% as shown in FIG. 1.

Experimental Example 2

Histamine Secretion Inhibition by *Illicium verum* Extract

MC/9 mouse mast cells were seeded in a 96-well plate and treated with 25 μg/ml compound 48/80 and the *Illicium verum* extract in pre-determined concentrations (0, 25, 50, 100, 200 and 400 μg/ml) for 20 min (Bytautiene et al., IgE-independent mast cell activation augments contractility of nonpregnant and pregnant guinea pig myometrium. Int Arch Allergy Immunol (2008) June 3, 147(2), 140-146; Kim et al. (Lithospermi radix extract inhibits histamine release and production of inflammatory cytokine in mast cells. Biosci Biotechnol Biochem (2007) December 7, 71(12), 2886-2892). Afterwards, the level of allergenic histamine which was secreted in medium was measured by the ELISA kit (Oxford Biomedical Research Inc., USA). The 100% productivity was calculated with referring to difference between the untreated group and the treated group with the compound 48/80.

The inhibition rate was calculated as follows:

[1−(the level of the secreted histamine in the treated group−the level of the secreted histamine in the untreated group)/(the level of the secreted histamine in the positive control−the level of the secreted histamine in the untreated group]×100.

All data were expressed as mean±standard deviation. Student's t-test was used to examine differences among groups and the data with $p<0.05$ were considered as statistically significant.

Figure 2:
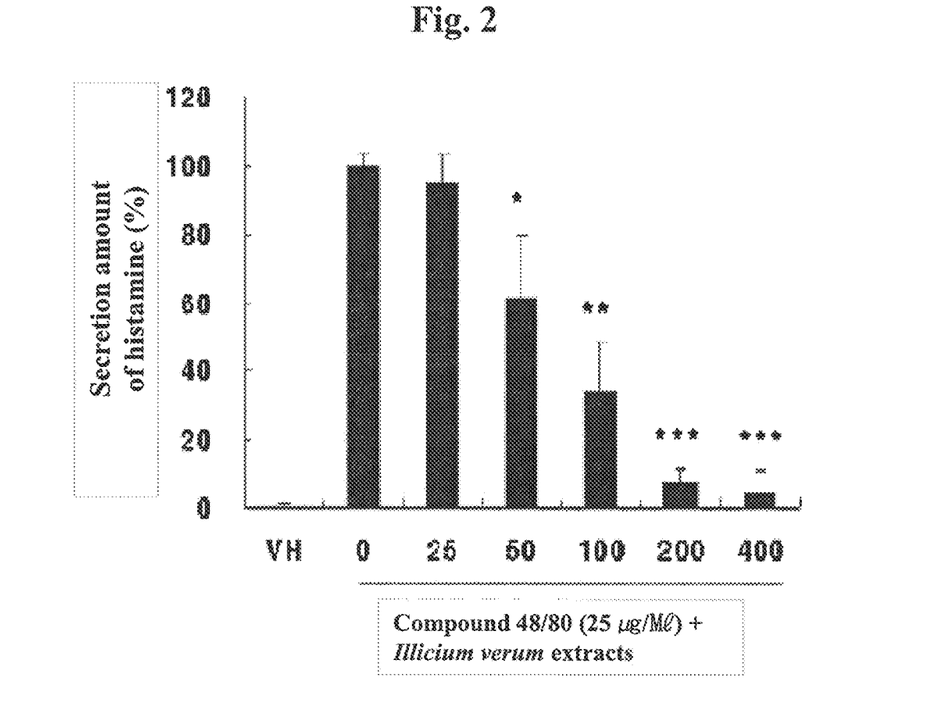
FIG. 2 represents the inhibitory effect on histamine secretion by the *Illicium verum* extract.

As results, we verified that the *Illicium verum* extract inhibited the secretion of the allergenic histamine in a dose-dependent manner as shown in Table 1 and FIG. 2. More specifically, the inhibition rate of the histamine secretion by the *Illicium verum* extract was analyzed to show 95.19 μg/ml of $IC_{50}$. In this regard, it would be understood that the *Illicium verum* extract has an excellent inhibition effect on allergenic histamine (Table 1 and FIG. 2).

TABLE 1

Allergenic histamine secretion inhibition by the *Illicium verum* extract

| Sample concentrations | Inhibition rate (%) |
|---|---|
| 25 μg/ml | 5.0% |
| 50 μg/ml | 38.4% |
| 100 μg/ml | 66.0% |
| 200 μg/ml | 92.2% |
| 400 μg/ml | 95.5% |

Experimental Example 3

Inhibitory Activities of the *Illicium verum* Extract to Cytokine Secretion

MC/9 mouse mast cells seeded in a 96-well plate were treated with 20 nM PMA (Phorbol Myristate Acetate) and 0.5 μM or 1 μM calcium ionophore A23187, together with various concentrations of the *Illicium verum* extract (0, 25, 50, 100, 200 and 400 μg/ml). The positive control was incubated with 10 nM dexamethasone (Dex) and 10 nM cyclosporine A (CsA). Seven hour later, the secreted amount of cytokines in medium was measured using the ELISA kit (R&D systems Inc., Minneapolis, USA). The 100% activity was calculated with referring to difference of the secreted cytokine amount between the untreated group and the treated group with PMA and A23187.

The secretion amount was calculated as follows:

[1−(the amount of the secreted cytokine in the treated group−the amount of the secreted cytokine in the untreated group)/(the amount of secreted histamine in positive control−the amount of the secreted histamine in the untreated group]×100.

The inhibition rate was calculated as follows:

[1−(the amount of the secreted cytokine in the treated group−the amount of the secreted cytokine in the untreated group)/(the amount of secreted cytokine in positive control−the amount of the secreted cytokine in the untreated group]×100.

All data were expressed as mean±standard deviation. Student's t-test was used to examine differences among groups and the data with $p<0.05$ were considered as statistically significant.

Figure 3:
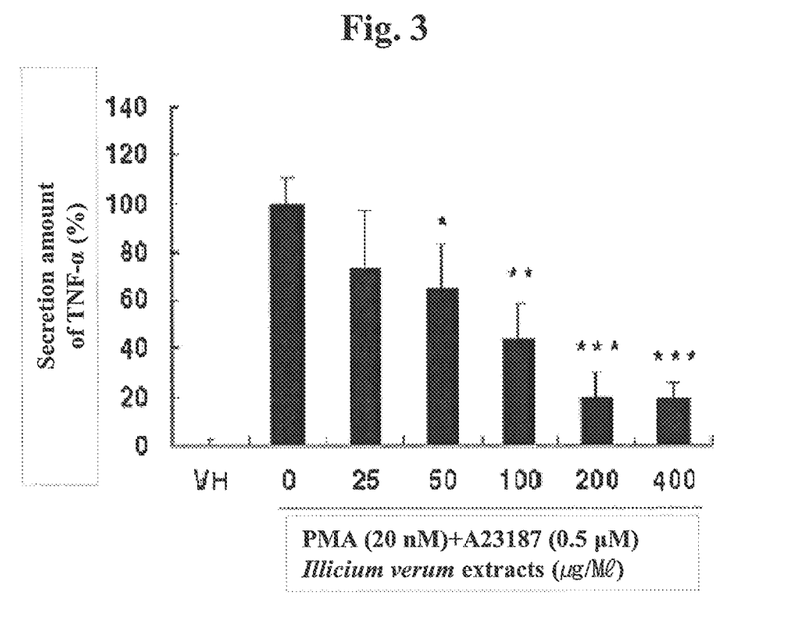
FIG. 3 represents the inhibitory effect on TNF-$\alpha$ secretion by the *Illicium verum* extract.

The measurement results of the secreted TNF-α demonstrated that the *Illicium verum* extract inhibits the secretion of allergenic TNF-α, as shown in Table 2 and FIG. 3.

TABLE 2

Allergenic TNF-α secretion inhibition by the *Illicium verum* extract

| Sample concentrations | Inhibition rate of TNF-α (%) |
|---|---|
| Positive control (CsA) | 46.1% |
| 25 µg/ml | 27.3% |
| 50 µg/ml | 35.7% |
| 100 µg/ml | 55.8% |
| 200 µg/ml | 79.9% |
| 400 µg/ml | 81.2% |

Figure 4:
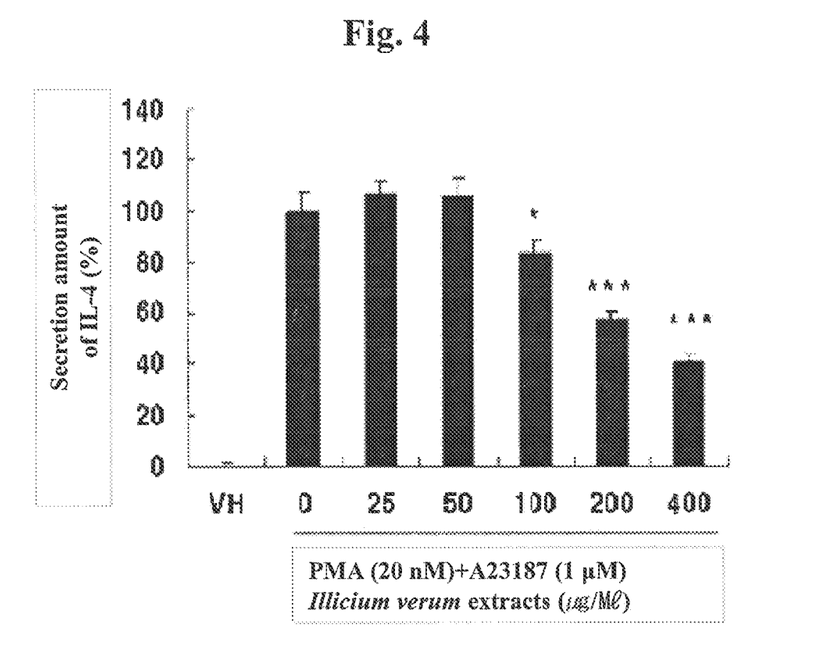
FIG. 4 represents the inhibitory effect on IL-4 secretion by the *Illicium verum* extract.

The results from measuring the secreted amount of IL-4 addressed that the *Illicium verum* extract inhibits the secretion of allergenic IL-4, as shown in Table 3 and FIG. 4.

TABLE 3

Allergenic IL-4 secretion inhibition by the *Illicium verum* extract

| Sample concentrations | Inhibition rate of IL-4 (%) |
|---|---|
| Positive control (Dex) | 0.4% |
| Positive control (CsA) | 23.7% |
| 25 µg/ml | −6.9% |
| 50 µg/ml | −6.4% |
| 100 µg/ml | 16.7% |
| 200 µg/ml | 43.0% |
| 400 µg/ml | 59.7% |

Figure 5:
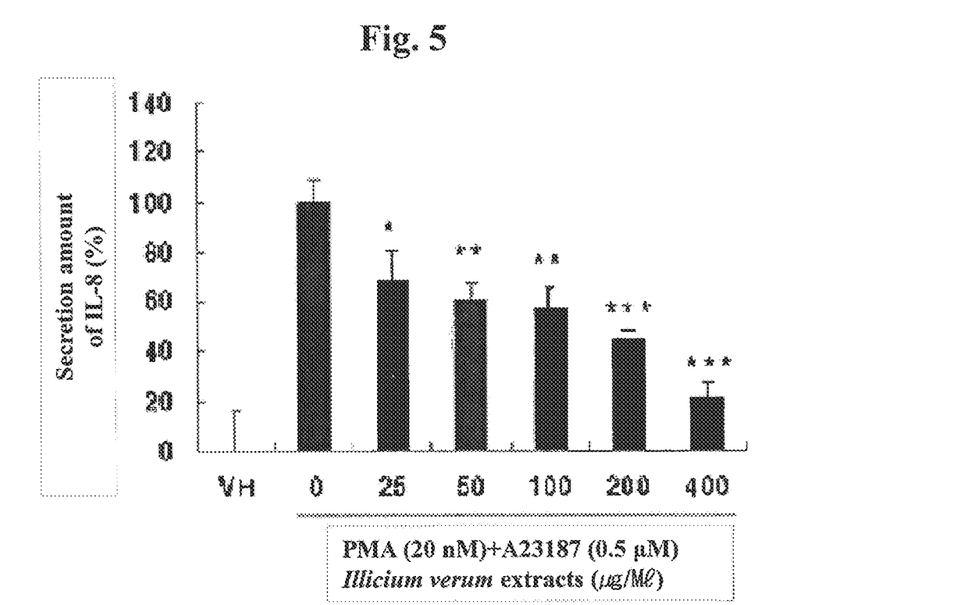
FIG. 5 shows the inhibitory effect on IL-8 secretion by the *Illicium verum* extract.

The results from measuring the secreted amount of IL-8 addressed that *Illicium verum* extract inhibits the secretion of allergenic IL-8, as shown in Table 4 and FIG. 5.

TABLE 4

Allergenic IL-8 secretion inhibition by the *Illicium verum* extract

| Sample concentrations | Inhibition rate of IL-8 (%) |
|---|---|
| Positive control (Dex) | 23.0% |
| Positive control (CsA) | 26.2% |
| 25 µg/ml | 32.0% |
| 50 µg/ml | 39.3% |
| 100 µg/ml | 42.6% |
| 200 µg/ml | 55.7% |
| 400 µg/ml | 78.7% |

Experiment Example 4

Inhibitory Activities of the *Illicium verum* Extract to Cytokine Secretion in Allergic Atopic Dermatitis Model 4-1. Experimental Animal and Care Condition 5.5-week old male NC/Nga mice purchased from Joongang Experimental Animal, Inc. which has been frequently used as animal models for allergic atopic dermatitis (Oshio et al., Dermatophagoides farinae extract induces severe atopic dermatitis in NC/Nga mice, which is effectively suppressed by the administration of tacrolimus ointment. *International Immunopharmacology* (2009), January 20, 9(4), 403-411) were kept at 20-22° C. and under 40-46% humidity and a 12-hr light/dark cycle intervals for 2 weeks adapted in animal breeding system of Korea Institute of Oriental Medicine. The mice were allowed food and water ad libitum and separated randomly into each 6 mice per group.

4-2. Preparation of Allergic Atopic Dermatitis Animal Model

For preparing the allergic atopic dermatitis animal model, the skin of 8-week old NC/Nga mice were coated with a house dust mite *Dermatophagoide farina* (DfE) extract (Biostir-AD, Astellas, Japan) as atopic inducing antigens to induce a dermatitis (Oshio et al., Dermatophagoides farinae extract induces severe atopic dermatitis in NC/Nga mice, which is effectively suppressed by the administration of tacrolimus ointment. *International Immunopharmacology* (2009), January 20, 9(4), 403-411). Before one day of the experiment, the hairs on the back and both ears of each mouse were shaved using a grainer (JD-S-138, THRIVE, Japan) and shave cream (veet, Reckitt benckiser, France). Afterwards, only grainer was used at applying the antigen. On day 0 of the experiment, the mice was topically treated with 150 µl of 4% SDS (Sodium Dodecyl Sulfate), kept to stand for 2-3 hr and treated with the *D. farina* antigen to each of the back (100 mg/mouse) and both ears (10 mg/mouse). The application of SDS and the antigen was performed twice a week for 3 weeks.

4-3. *Illicium verum* Extract Treatment to Allergic Atopic Dermatitis Animal

For verification of the anti-allergic effect of the positive control (Protopic ointment, Astellas Pharma Inc., USA) and the *Illicium verum* extract, 1000 µg/mouse of the *Illicium verum* extract dissolved in 70% ethanol solution was applied to the back and the ears of the experimental mice before 30 min of induction of allergic atopic dermatitis in Experimental Example 4-2 and then applied everyday for 3 weeks after 5 days of the antigen application.

Figure 6:
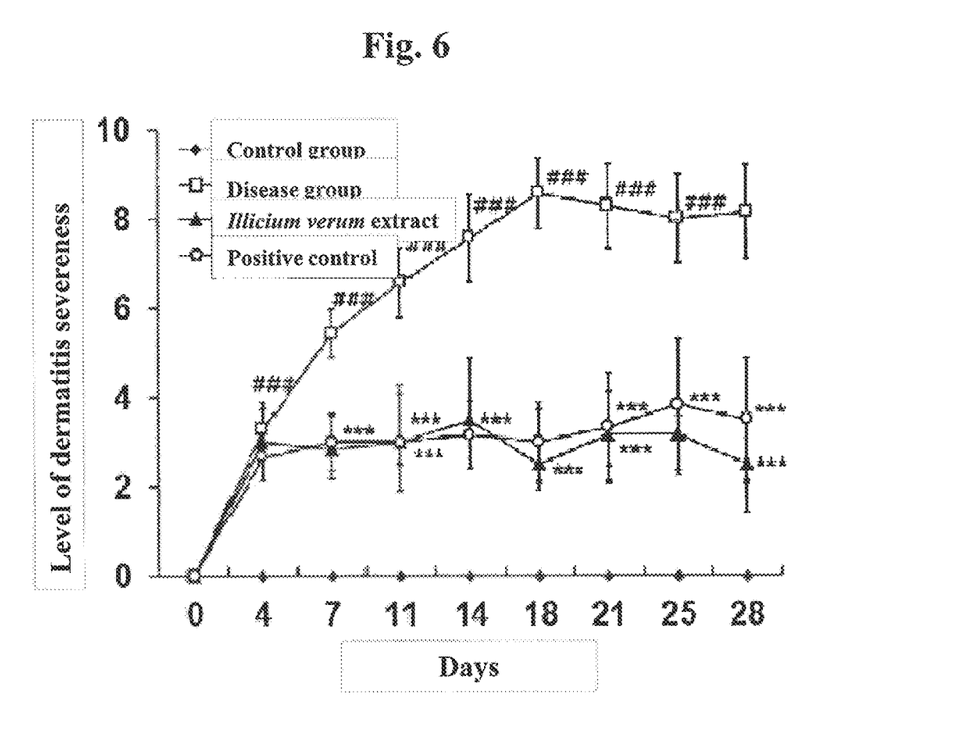
FIG. 6 shows the in vivo treatment efficacies on atopic dermatitis by the *Illicium verum* extract.

4-4. Analysis of Dermatitis Inhibition Effect in Allergic Atopic Dermatitis Animal The extent of a skin damage of the allergic atopic dermatitis mice treated with the *Illicium verum* extract in Experimental Example 4-3 was tested twice a week 30 min before the extract application. Erythema/hemorrhage, edema, excoriation/erosion and scarring/dryness were evaluated by the three scores as 0 (none), 1 (mild), 2 (moderate), and 3 (severe) as known to those ordinarily skilled in the art (Yamamoto et al., A novel atopic dermatitis model induced by topical application with dermatophagoides farinae extract in NC/Nga mice. *Allergology International* (2007), May 1, 56(2), 139-148). It was revealed that the *Illicium verum* extract reduced atopic dermatitis to the similar extent to the positive group (FIG. 6).

4-5. Inhibition Effect of Ear Edema in Allergic Atopic Dermatitis Animal

The thickness of the ear of the mice treated as Experimental Example 4-3 was measured using a Dial thickness gauge (M110-25, Mitutoya, Japan) twice a week, which was considered as allergenic edema indicator. All data were expressed as mean±standard deviation. Student's t-test was used to examine differences among groups and the data with $p<0.05$ were considered as statistically significant.

As results, the final ear thickness of the negative control and the disease group treated with the antigen was measured 0.29 mm and 1.28 mm, respectively. The thickness of the mice ear treated with the *Illicium verum* extract was analyzed 0.56 mm, representing dramatic inhibition effect on the ear edema. Meanwhile, the ear thickness of the positive control was measured 0.61 mm ($p<0.05$).

Figure 7:
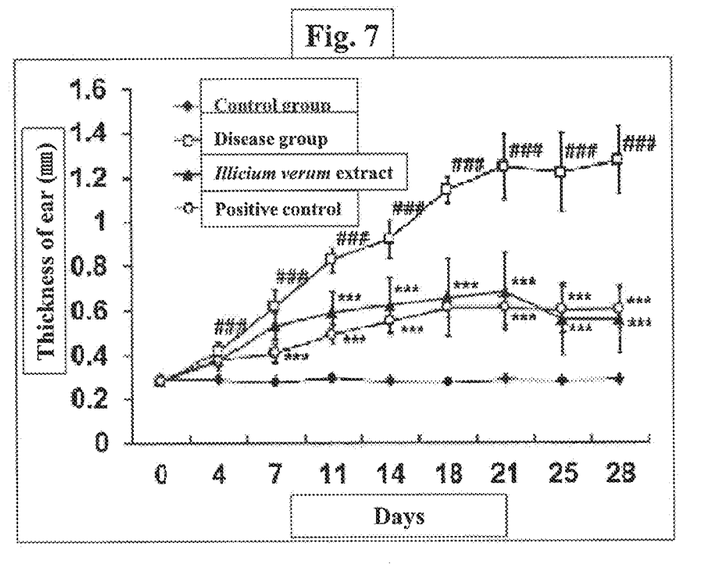
FIG. 7 shows the in vivo treatment efficacies on ear edema by the *Illicium verum* extract.

The results urge us to reason that the *Illicium verum* extract has an excellent inhibition effect on the ear edema (FIG. 7).

4-6. Decrease in Epidermal Layer of Allergic Atopic Dermatitis Animal and Evaluation of Inhibition Effect on Infiltration of Inflammatory Cells by *Illicium verum* Extract The skin tissues from the ear or back of the mice treated as Experimental Example 4-3 were trimmed in a certain thickness, subjected to a general tissue processing, embedded in paraffin and sectioned at 2-3 μm. The sections were stained with hematoxylin and eosin solution (HE) for histopathological analysis of the lesion tissues.

Figure 8:
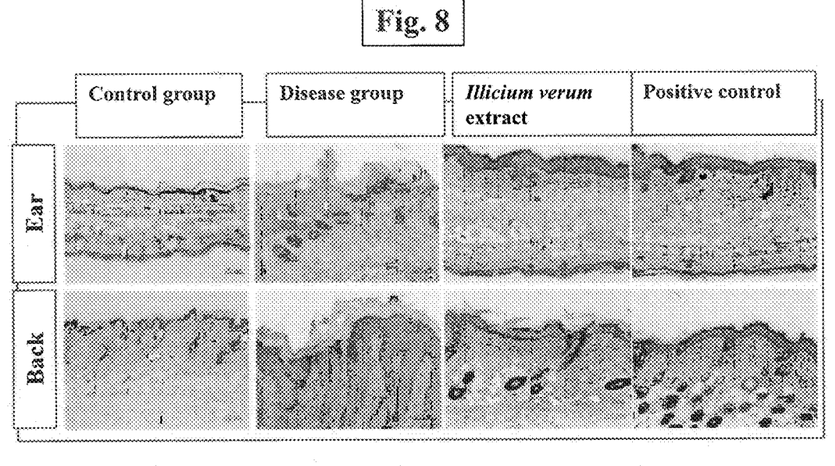
FIG. 8 represents the epidermal thickness reduction and the cell infiltration inhibitory effect by the *Illicium verum* extract.

The inflammatory cell infiltration and epidermis thickening were observed in the antigen-treated mice, addressing the induction of atopic dermatitis. The skin tissue of the mice treated with the *Illicium verum* extract was analyzed to show reduced symptoms such as inflammatory cell infiltration and epidermis thickening, demonstrating that the *Illicium verum* extract has inhibition effects on atopic dermatitis (FIG. 8).

4-7. Decrease in IgE Concentration in Serum of *Illicium verum* Extract-Treated allergic Atopic Dermatitis Mice The blood sample was pooled from the mice treated as Experimental Example 4-3 and the total IgE concentration was analyzed using the IgE ELISA kit (Shibayagi Co Japan) and a microplate reader.

The IgE concentrations in the serum of the normal group and the disease group were 104.56 ng/ml and 2050.25 ng/ml, respectively. The IgE concentrations in the serum of the *Illicium verum* extract-treated group and the positive control group were reduced to 528.24 ng/ml and 1006.47 ng/ml, respectively.

Figure 9:
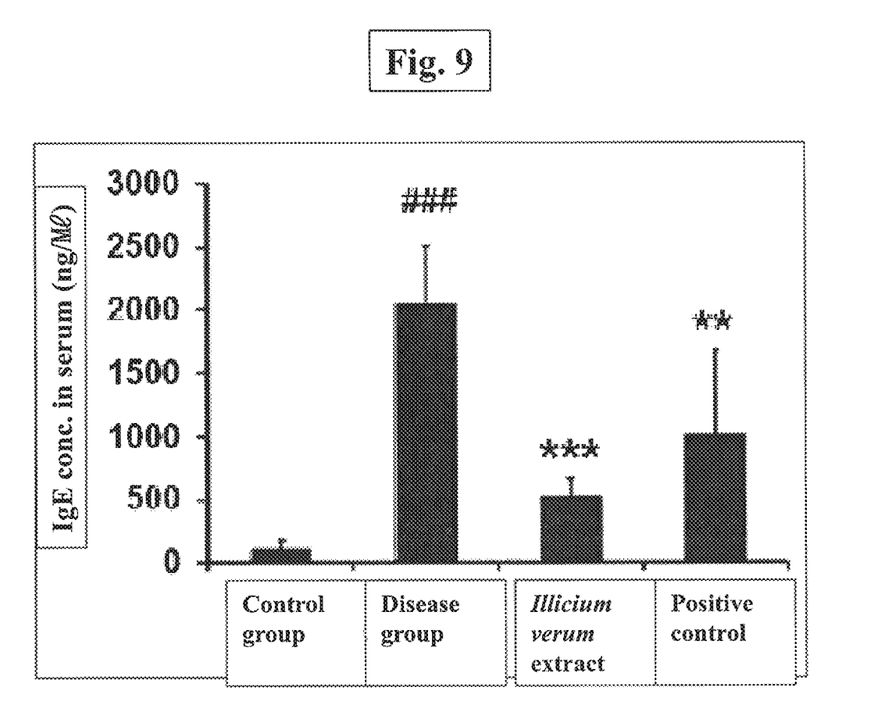
FIG. 9 represents the IgE reduction effect in mouse serum by the *Illicium verum* extract.

Accordingly, it would be recognized that the *Illicium verum* extract has IgE inhibition effect in the serum (FIG. 9).

What is claimed is:

1. A method for treating an allergic disease, comprising administering to the skin of a subject a composition comprising a solvent extract from *Illicium verum* as the only active ingredient against allergic disease of the composition.

2. The method according to claim 1, wherein the allergic disease is selected from the group consisting of edema, anaphylaxis, allergic rhinitis, asthma, allergic conjunctivitis, allergic dermatitis, atopic dermatitis, contact dermatitis, urticaria, pruritus, insect allergy, alimentary allergy, and drug allergy.

3. The method according to claim 1, wherein the composition is a cosmetic composition.

4. The method according to claim 1, wherein the allergic disease is edema.

5. The method according to claim 1, wherein the allergic disease is anaphylaxis.

6. The method according to claim 1, wherein the allergic disease is allergic rhinitis.

7. The method according to claim 1, wherein the allergic disease is asthma.

8. The method according to claim 1, wherein the allergic disease is allergic conjunctivitis.

9. The method according to claim 1, wherein the allergic disease is allergic dermatitis.

10. The method according to claim 1, wherein the allergic disease is atopic dermatitis.

11. The method according to claim 1, wherein the allergic disease is contact dermatitis.

12. The method according to claim 1, wherein the allergic disease is urticaria.

13. The method according to claim 1, wherein the allergic disease is pruritus.

14. The method according to claim 1, wherein the allergic disease is insect allergy.

15. The method according to claim 1, wherein the allergic disease is alimentary allergy.

16. The method according to claim 1, wherein the allergic disease is drug allergy.

17. The method according to claim 1, wherein the composition is in the form of a paste.

18. The method according to claim 1, wherein the composition is in the form of a gel.

19. The method according to claim 1, wherein the extract is obtained using a solvent selected from the group consisting of (a) water, (b) C1-C4 anhydrous or hydrous lower alcohol, (c) a mixture solvent of the lower alcohol with water, (d) acetone, (e) ethylacetate, (f) chloroform, (g) 1,3-butylene glycol, (h) hexane, (i) diethyl ether, and (j) butyl acetate.

20. The method according to claim 19, wherein the C1-C4 anhydrous or hydrous lower alcohol is selected from the group consisting of methanol, ethanol, propanol, butanol, n-propanol, isopropanol, and n-butanol.

* * * * *